(12) United States Patent
Kendig et al.

(10) Patent No.: US 8,834,687 B2
(45) Date of Patent: Sep. 16, 2014

(54) MULTILAYER SELF-DECONTAMINATING COATINGS

(75) Inventors: Martin W. Kendig, Thousand Oaks, CA (US); Young J. Chung, Calabasas, CA (US); Alan B. Harker, Thousand Oaks, CA (US); Dennis R. Strauss, Ventura, CA (US); Walther Ellis, Logan, UT (US); Linda S. Powers, Logan, UT (US)

(73) Assignee: Teledyne Licensing, LLC, Thousand Oaks, CA (US)

( * ) Notice: Subject to any disclaimer, the term of this patent is extended or adjusted under 35 U.S.C. 154(b) by 1944 days.

(21) Appl. No.: 11/529,787

(22) Filed: Sep. 28, 2006

(65) Prior Publication Data

US 2012/0111719 A1    May 10, 2012

Related U.S. Application Data

(60) Provisional application No. 60/722,567, filed on Sep. 30, 2005.

(51) Int. Cl.
| | |
|---|---|
| *C25B 9/00* | (2006.01) |
| *A61L 2/00* | (2006.01) |
| *A61L 2/03* | (2006.01) |
| *A61L 2/20* | (2006.01) |
| *A61L 2/235* | (2006.01) |
| *C02F 1/467* | (2006.01) |

(52) U.S. Cl.
CPC .............. *A61L 2/0011* (2013.01); *C02F 1/4674* (2013.01); *A61L 2/0094* (2013.01); *A61L 2/035* (2013.01); *A61L 2/20* (2013.01); *A61L 2202/26* (2013.01); *A61L 2/235* (2013.01)
USPC ............................ 204/242; 204/252; 204/262

(58) Field of Classification Search
USPC .................................................. 204/242, 252
See application file for complete search history.

(56) References Cited

U.S. PATENT DOCUMENTS 4,583,548 A * 4/1986 Schmid ........................ 600/396
4,798,870 A   1/1989 Lyle, Jr. et al. ............ 525/327.1
(Continued)

FOREIGN PATENT DOCUMENTS

JP         60249265 A    12/1985
WO   WO 0128598 A     4/2001
(Continued)

OTHER PUBLICATIONS

U.S Patent Application Publication No. 2003/0009127 A1; Jan. 9, 2003; Trescony et al.

(Continued)

*Primary Examiner* — Arun S Phasge
(74) *Attorney, Agent, or Firm* — Koppel, Patrick, Heybl & Philpott

(57) ABSTRACT

A layered construction for use in decontaminating a surface or enclosed space is described. The construction is an electrochemical cell which includes a cathode, an electrolyte layer, an anode and a protective surface layer. A precursor compound that can be electrically decomposed to release an oxidant, on demand and over an extended period of time, is included in the layered structure, preferably in the electrolyte layer. The oxidant compounds react with various different chemical or biological contaminants in contact the protective layer, thereby deactivating, destroying or devitalizing the contaminants. The layered construction is suitable for application to a device or substrate, or placement in an enclosed space, and can be used on sensitive surfaces such as electronic components and human skin.

15 Claims, 6 Drawing Sheets

(56) References Cited

U.S. PATENT DOCUMENTS

| | | | |
|---|---|---|---|
| 5,154,920 A | 10/1992 | Flesher et al. | 514/643 |
| 5,236,703 A | 8/1993 | Usala | 424/78.36 |
| 5,250,160 A | 10/1993 | Oksman et al. | 204/131 |
| 5,252,291 A | 10/1993 | Tsao | 422/23 |
| 5,431,908 A | 7/1995 | Lund | 424/78.1 |
| 5,639,452 A | 6/1997 | Messier | 424/78.1 |
| 5,665,492 A | 9/1997 | Sotomura | 429/213 |
| 6,057,488 A | 5/2000 | Koper et al. | 588/200 |
| 6,315,886 B1 * | 11/2001 | Zappi et al. | 205/701 |
| 6,482,309 B1 * | 11/2002 | Green et al. | 205/619 |
| 6,555,055 B1 | 4/2003 | Cisar et al. | 422/28 |
| 6,562,885 B1 | 5/2003 | Moorehead et al. | 524/80 |
| 6,566,574 B1 | 5/2003 | Tadros et al. | 588/200 |
| 7,033,509 B2 | 4/2006 | Klein et al. | 210/753 |
| 7,172,734 B1 * | 2/2007 | Joshi | 422/186 |
| 2004/0045479 A1 | 3/2004 | Koper et al. | |
| 2004/0109853 A1 | 6/2004 | McDaniel | |

FOREIGN PATENT DOCUMENTS

| | | |
|---|---|---|
| WO | WO 0200267 A | 1/2002 |
| WO | WO 2008018856 A | 2/2008 |

OTHER PUBLICATIONS

Zelazowska, Elzbieta at al., "Sol-gel derived Li-ion conducting polymer electrolytes", Materials Science—Poland, vol. 23, No. 1, p. 177-194 (2005).

PCT Notification of The International Search Report and The Written Opinion of The International Searching Authority, Dated Jul. 7, 2008; for International Application No. PCT/US2006/027751.

A. Alimova, A. Katz, P. Gottlieb, and R. R. Alfano, "Proteins and Dipicolinic Acid Released During Heat Shock Activation of *Bacillus subtilis* spores probed by Optical Spectroscopy": Applied Optics. 45:445-450: 2006.

* cited by examiner

MULTILAYER SELF-DECONTAMINATING COATINGS

CROSS REFERENCE TO RELATED APPLICATION

This application claims priority to the earlier provisional application entitled "MULTILAYER SELF-DECONTAMINATING COATINGS," Ser. No. 60/722,567, filed Sep. 30, 2005, the disclosures of which are hereby incorporated herein by reference.

STATEMENT AS TO FEDERALLY SPONSORED RESEARCH

This invention was made with Government support under HR0011-04-C-0131 awarded by the Defense Advanced Research Projects Agency (DARPA). The Government has certain rights in this invention.

BACKGROUND

1. Field of the Invention

The present invention relates primarily to a multi-layered electrically activated coating or appliqué applied to devices or substrates, particularly electronic and circuit components which can be automatically activated, or activated at the option of the user, to release an oxidizing agent to decontaminate the surface of the substrate or device while not being destructive of the underlying substrate or the surrounding environment. In particular, the oxidizing agent is effective in deactivating or substantially reducing the effectiveness of certain chemically and biologically active agents that it comes in contact with. The coating or cell can also be readily reactivated after activation and depletion. The invention also provides a multi-layered electrolytic cell which, even in the absence of aqueous media, can release controlled amounts of a decontaminating agent into an enclosed space.

2. Description of the Related Art

The surfaces of devices, and particularly electronics enclosed within or behind a protecting structure such as a control panel or a enclosing case, are particularly difficult to decontaminate once exposed to contaminating or toxic chemical or biological agents. The difficulties arise in part from the inability to gain access to the enclosed space and, even where access can be accomplished, from the need to introduce decontaminating agents into small spaces in or behind the devices or components thereof. Still further, many decontaminating agents are delivered as aqueous solutions. The aqueous solvent can also be detrimental to the functionality of the device being decontaminated, causing the electrical components to short circuit and metal components to oxidize (rust).

There are numerous examples of decontamination agents that can be applied to a contaminated surface after the surface has been exposed to a contaminant. For example, U.S. Pat. No. 6,566,574 covers a composition including a solubilizing agent for the contaminant, particularly cationic surfactants, and at least one reactive compound that attacks or neutralizes the contaminant. Published U.S. Application 2004/0045479, and its parent U.S. Pat. No. 6,057,488, discloses the use of finely divided metal oxides of hydroxides, which are applied to contaminated surfaces. There are also examples of coatings of various different compositions. For example, U.S. Application No. 2004/0109853 discloses a coating containing a phosphoric acid triestester hydrolase. In addition, U.S. Pat. No. 6,566,574 to Tadros et al. discloses materials delivered as foams, sprays, liquids, fogs or aerosols to neutralize chemical or biological agents already contaminating a surface.

Treatments using resins containing decontamination agents have been described. U.S. Pat. No. 6,562,885 to Moorehead et al. is directed to a substance capable of devitalizing hazardous biological agents and deactivating hazardous chemical agents comprising an activated anion exchange resin having a particle size in the range of about 0.1-300 microns, the resin particles being iodinated by exposure to a sufficient amount of an iodine-substance absorbable by the anion exchange. The resin particles absorb the iodine-substance converting the resin particles into activated resin particles. The iodine-substance is selected from the group consisting of $I_2$ (i.e., diatomic iodine), and polyiodide ions having a valence of $-1$. The activated resin particles are placed into contact with the biological or chemical agent after contamination as a dry aerosol, by dust coating, or by admixing the particles with a carrier to form a coating. The activated resin particles can also be applied to the surface of an object, providing a continuously active coating (active once applied; can not be activated at-will or when the contamination is present).

U.S. Pat. No. 5,639,452 to Messier discloses a disinfectant substance comprising an iodine impregnated ion exchange resin which is a demand-type broad spectrum resin-polyiodide disinfectant useful in sterilizing fluids, and particularly a polyiodide that leaves behind nondetectable or otherwise acceptable residual diatomic iodine in treated fluids. U.S. Pat. No. 5,431,908 to Lund also teaches a method of preparing halide-impregnated ion exchange resins useful in purifying fluids such as water.

Polymeric decontaminations systems have also been described. U.S. Pat. No. 5,236,703 is directed to a polymeric substrate, such as rubber or latex, which incorporates povidone-iodine which acts as a controlled release biologically active agent. U.S. Pat. No. 5,154,920 discloses a liquid disinfectant composition which can be used to coat surfaces of a substrate with a polymeric film to impart prolonged germicidal properties to the coated surface by inclusion of phenols, or quaternary ammonium salts. U.S. Pat. No. 4,798,870 is directed to hydrohalide-polyhalides or quaternary halide-perhalide salts which are bound to polymeric surfaces, such as a fabric or polymer film, using a vinylpyridine as a binding agent. Disinfectant patches have been constructed using conventional technology in which nano-silver (nano-Ag) particles or quaternary ammonium compounds are included in the absorbent gauze dressing.

Electrochemically-generated oxidants such as peroxides, hypohalites, and high valent halogens (halogen gases and halo-oxides) can also be effective decontamination agents. The industrial production of chlorine bleach (NaOCl) by the electrolysis of brine, for example, employs electrolytic formation of chlorinated disinfectants. These techniques typically use aqueous solutions, usually held within a container, that build up electrochemically-generated oxidants either on or in an object placed in the solution, as described in U.S. Pat. Nos. 5,250,160 and 6,555,055. They have also been used to purify other bodies of liquids such as streams or pools of water, as described in U.S. Pat. No. 7,033,509.

However, each of these references suffers from one or more of the following disadvantages: the active ingredients are external and must be placed in physical contact with the contaminated surface of the object in order to decontaminate it; the composition or resin is active once applied but can not be activated on demand; the active ingredients are difficult to regenerate if depleted; the systems or coatings used for decontamination are inflexible; the oxidizing agent generated is too acidic or too strong an oxidant to be used in many types of applications (e.g. chlorine or chloride), including the disinfection of electronics and sensitive surfaces such as human skin; the solvents or carriers used to deposit, dissolve, or suspend the active ingredients are detrimental to the functionality of the object or device being treated; the addition of liquid disinfectants requires an additional step in the treatment protocol; the decontaminating surfaces are prone to fouling (i.e. buildup of an overlayer of biological or other types of debris) which leads to a loss of activity; inclusion of active halogens in a dressing is problematic owing to the unstable highly reactive state of the active halogen or halogenated compound; activation of the system is hazardous to the environment or to human health or safety; or the technique requires an enclosed space filled with water or aqueous media, heavy or bulky equipment, or is too costly for remote or application.

SUMMARY

The present invention is directed to a non-destructive, electrically-activated layered construction providing decontamination to an adjacent surface or enclosed space. The layered structure may include a cathode, an electrolyte layer, an anode and a protective surface layer. The system can be activated on demand, actively decontaminating over an extended period of time, and readily regenerated after activation and depletion. In one embodiment of the invention, activation of the system releases an oxidizing agent effective in deactivating chemically or biologically active agents at or near the surface. In another embodiment, a precursor compound that can be electrically decomposed to release an oxidant is included in the layered structure, preferably in the electrolyte layer. In yet another embodiment of the invention, an enclosed space can be decontaminated in the absence of liquids, particularly aqueous media. In a further embodiment, the precursor compound can release halogen ions which react with various different chemical or biological contaminants that may contact the protective layer, thereby destroying, or devitalizing the contaminants. In yet another embodiment, heating the cell surface prior to electrolysis can facilitate the decontamination of resistant contaminants.

The invention may be useful for many types of applications including disposable dressings for military or first responder use in treating wound victims, burn victims, and skin infections (e.g. athlete's foot). Most importantly, the invention can be used to deliver a disinfectant on demand rather than using a liquid containing a continually active oxidant. Although the latter approach may be effective in some situations, it can also lead to overexposure which can kill human cells. In contrast, the present invention includes an electrochemically generated oxidant which ceases to evolve once the current is turned off and can be activated only when needed. In addition, surfaces coated with the present invention are easily regenerated if depleted, and are not prone to fouling.

DETAILED DESCRIPTION

Figure 1:
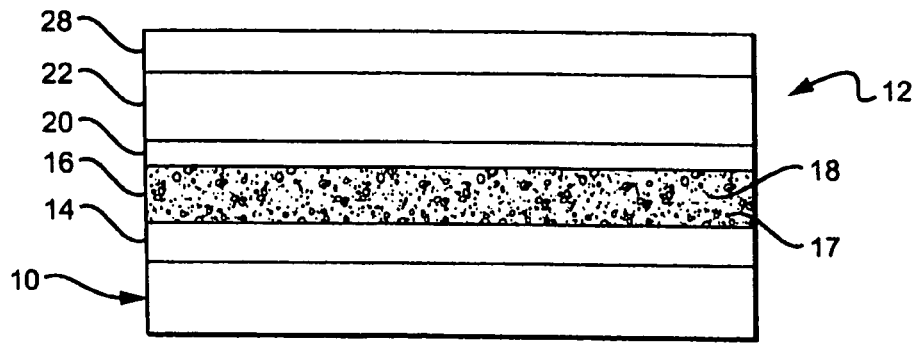
FIG. 1 is a schematic drawing of a device, structure or substrate including a coating comprising a multilayered electrochemical cell incorporating features of the invention.

The invention relates to a structure containing devitalizing agent or disinfectant that can be applied as a coating to objects or provided as free standing delivery means, which is capable of decontaminating adjacent objects or surfaces. The coating or delivery means may be inert when applied to the object, and then automatically or manually activated once a contaminating chemical or biological agent is detected. The invention also includes structure necessary for activating the coating or delivery means and may further include sensors to detect contamination of the surface which, in turn, cause the decontaminating ingredients to be released. Such a substance and structure can be used, for example, to decontaminate solid surfaces, substrates, or mechanical and electronic devices that are exposed to biological agents such as airborne pathogens and chemical agents, and may do so whether exposure is continuous or intermittent and without detriment to the surface or object being treated.

The coating could also be used to provide a protective barrier on such surfaces and devices that are likely be exposed to biological and chemical agents, such that they can be devitalized on demand without significant detriment to the device's usual utility, requiring an external supply of decontamination substances (at least until the active agent present in the coating has been exhausted), or using additional decontaminating procedures after exposure to the agent. Such a protective coating can also be useful on objects that are likely to be exposed to contaminating agents on a more or less regular basis, for example, equipment used in medical emergency response or other health care applications, or surfaces in public facilities.

The coating and activating structure is also useful on objects that may be exposed to such agents in the event of a catastrophe, such as a military conflict, terrorist incident or a hazardous material spill. Devices which can be decontaminated by the invention include without limitation electronic devices such as light emitting devices (LEDs), sensors, and fuel cells. Similarly, the invention could be mounted on or within a variety of structures for decontamination purposes, including without limitation medical equipment, mobile military equipment, and electronic devices. Substrates which can be decontaminated by the invention include device substrates, clothing, and dressings or bandages. A need exists for a rapidly applied adhesive patch to protect wounds from infection in hazardous environment such as the battlefield, for example.

Other features and advantages of the invention will be apparent from the following detailed description when taken together with the drawings, and from the claims. The following description presents preferred embodiments of the invention representing the best mode contemplated for practicing the invention. This description is not to be taken in a limiting sense but is made merely for the purpose of describing the general principles of the invention whose scope is defined by the appended claims.

Before addressing details of embodiments described below, some terms are defined or clarified. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. However, the following definitions refer to the particular embodiments described herein and are not to be taken as limiting; the invention includes equivalents for other undescribed embodiments. In addition, the materials, methods, and examples are illustrative only and not intended to be limiting.

As used herein, the term "adjacent to" when referring to a layer or coating on a surface, does not necessarily mean that the coating is immediately next to the surface; there may or may not be another contiguous or non-contiguous layer or material present between the layer or coating and the surface.

As used herein, the term "adjoining atmosphere" is intended to mean the atmosphere which lies next to or in contact with the surface.

As used herein, "biological agent" or "biological contaminant" refers to hazardous biological organisms or biological warfare (BW) agents including without limitation viruses, bacteria, fungi and unicellular parasites in any form, and biologically generated toxins.

As used herein, "chemical agent" or "chemical contaminant" means a hazardous chemical compound, including but not limited to chemical warfare (CW) agents and industrial or agricultural chemical compounds which may be hazardous.

As used herein, the term "contaminant" is intended to mean a biological or chemical contaminant.

As used herein, the term "deactivate" refers to the ability to render any chemical agent inactive, ineffective, or substantially less effective for its intended purpose, and particularly agents hazardous to human, life or health.

As used herein, the term "decontaminate" or "decontaminating" when referring to a surface or enclosed space is intended to mean deactivating or devitalizing, respectively, any chemical or biological agents present on a targeted surface or within a targeted space after exposure to such an agent.

As used herein, the terms "deposit", "depositing" or "deposited" when referring to material or layer deposition is intended to mean any standard means for deposition which does not affect the activity of the material or layer, including without limitation brushing, rolling, spraying, pouring, spin coating, dip coating, and printing. A coating or layer thus formed may have various types of structures or characteristics including without limitation coatings which are uniform, patterned, contiguous, noncontiguous, surface-layered or embedded. Furthermore, the depth of electrolyte penetration on or after deposition may vary depending upon the nature of the electrolyte, layer, surface, substrate (e.g. fabric), or process used, such that the resulting layer can be, without limitation, filled, covered, or impregnated with electrolyte.

As used herein, the term "decontaminate" or "decontaminating" when referring to a surface or an enclosed space is intended to mean devitalizing or ridding part or all the surface or space of contamination after exposure to one or more toxic agents, including without limitation chemical or biological agents.

As used herein, the term "devitalize" when used to describe a biological agent is intended to mean that the agent is destroyed, rendered totally inactive, or made substantially less effective. An agent may be devitalized in a number of ways including, without limitation, oxidation, disinfection or decomposition.

As used herein, the term "electrochemical cell" is intended to mean an electrochemical system comprising at least one anode and at least one cathode in mutual contact with at least one electrolyte.

As used herein, the term "halogen" is intended to mean an element located in Group VIIA of the periodic table including without limitation iodine.

As used herein, the term "on demand" when referring to activation of a decontamination system is intended to mean that the system can be activated or deactivated at-will, including without limitation continual activation, activation at or shortly after the time of exposure to contamination, or deactivation following a period of time after exposure.

As used herein, the term "independent" when referring to an electrochemical cell is intended to mean that the cell is operating or capable of operating independently of the surface or enclosed space being treated.

As used herein, the term "surface" when referring to the surface of an object is intended to mean the exterior or upper boundary of an object or body including the adjoining atmosphere.

As used herein, the term "surface contaminant" is intended to mean a contaminant on or within the surface of an object.

Compositions incorporating the features described herein can be applied to substrates to form a protective coating thereon. They can be admixed with a suitable carrier and the resultant coating applied to a substrate by any suitable means, for example, brushing, rolling, spraying, pouring or the like. The carrier may be a paint-type coating such as a water- or organic solvent-based or a polymeric material. Alternatively the composition can be applied on top of an adhesive previously coated on a non-stick carrier, such as a polymer film. The composition with adhesive (an adhesive backed appliqué) can then be removed from the carrier and applied to desired surface, with the adhesive contacting that surface. A decontaminating bandage or bag, for example, could be prepared in this manner. A multilayer coating according to the invention may be deposited or placed on a material (e.g., the inside of a bag) that is near a surface to be decontaminated, for example. Preferably, the material could be placed about 0.1 to about 4 inches from the surface. A bag of this type could be used to treat an appendage such as a foot, or for decontaminating a medical instrument. Alternatively, the coating could be deposited or placed directly on a bandage which might then be placed adjacent to, or in contact with, a surface such as skin.

The coatings as described herein are effective against chemical warfare agents and other chemical agents, particularly those susceptible to oxidation, hydrolysis, or nucleophilic attack by molecular halogens ($X_2$) or their hypohalite hydrolysis products ($OX^-$). It is important to note that the current clean-up procedure, recommended by the U.S. Government for decontamination of chemical warfare agents, uses aqueous chlorine bleach (NaOCl in water) as the active decontaminating agent.

These and other objects of the present invention will be apparent from the specification that follows and the appended claims. Attention is now directed to more specific details of embodiments that illustrate but not limit the invention.

Referring to FIG. 1, in a particular embodiment, a device, structure or substrate 10 includes a coating comprising a multilayered electrochemical cell 12 incorporating features of the invention comprising,
1) a cathode 14 comprising a first conductive coating layer applied to the device, structure or substrate 10,
2) a second layer (the electrolyte layer) 16 on the cathode 14 containing a compound 18 in a surrounding matrix 17, the compound 18 producing a decontaminating oxidant under suitable conditions of polarization,
3) a porous, conductive anode 20, and
4) a porous surface layer 22 which may be hydrophobic, or optionally include a hydrophobic or partially hydrophobic surface coating 28. An example of a partially hydrophobic surface suitable for use in the present invention is a patterned surface with non-hydrophobic pattern portions.

The electrolyte layer 16 preferably contains a non-hydroscopic solid, semi-solid (gel) or matrix which includes a liquid entrapped therein, the layer being ionically conducting but electrically non-conducting. The ionic characteristics of the electrolyte layer 16 may be provided by precursor chemical compounds (e.g. halides) which can release a reactive oxidizing reagent, including without limitation a molecular halogen, polyhalide anion, halogen cation, or hypohalite once activated. However, at the same time, the matrix of the electrolyte layer 16 should preferably be electrically nonconducting (electrically insulating), porous, and chemically stable in the presence of the generated oxidant. Polyethylene oxide, Nafion (a perfluorinated polymer) and crystalline $RbAg_4I_5$ are examples of suitable solid electrolytes. However, one skilled in the art will recognize that other solid electrolytes can be used. Examples of suitable ionic semi-liquid gels suitable for use in the invention include, but are not limited to, polyacrylonitrile, tetrapropyl ammonium iodide, ethylene carbonate, propylene carbonate, materials used in dye sensitive solar cells and electrochromic glass, quaternary alkyl ammonium in alkyl carbonate/polyacrylonitrile (PAN) gels with organic solvents, and solgels derived from porous silica gels such as Ormolyte (i.e. formed from tetraethyl orthosilicate and polyethylene glycol) which are each doped with an ionic liquid containing the halide salt.

The cathode 14 is preferably formed of a depolarizable and reversible material, examples of which may include various conducting polymers, disulfide polymers and ion insertion materials. Examples include, but are not limited to
1) metal/metal hydride combinations ($M+2H^+\rightarrow MH_2$)
2) materials which undergo a cation insertion procedure such as
Prussian Blue or materials into which metallic ions can be intercalated

$M^+ + ne^- + WO_3 \rightarrow M_nWO_3$

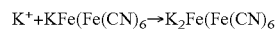
$K^+ + KFe(Fe(CN)_6) \rightarrow K_2Fe(Fe(CN)_6)$ $Li^+$ insertion is not preferred because of its hygroscopic nature; $K^+$ is a more suitable alternative.
3) Conducting polymers such as composites of polyaniline and 2,5 dimercapto-1,3,4 thiadiazole, or PANI-iodide.
Alternatively, a depolarizable cathode may not be needed for applications requiring only short electrolysis times.

The anode 20 is preferably a stable, porous metal, electrically conducting oxide or a conductive composite which may be applied by standard coating or printing techniques on a surface or a fabric which incorporates the electrodes and electrolyte. The term "stable" means that the anode is not detrimentally modified by the oxidant that is generated. The anode material must also enable halide oxidation. Materials used as fuel cell anode materials are, for example, suitable in this application. The anode can be either or both a photo-anode and an electro-anode. A suitable, non-limiting example is palladium (Pd) coated, dye sensitive, titanium dioxide ($TiO_2$). A preferred technique of depositing the anode material on a fuel cell assembly is screen printing. It may be desirable to also include a basic, porous polymer layer to induce hydrolysis of diffusing halogen molecules to their hypohalite analogs.

The porous surface layer 22 can be a permeable film or membrane which serves to transport the electrochemically generated oxidant to the surface where it reacts with the chemical or biological agent to decontaminate the surface of the assembled structure. The membrane material is preferably hydrophobic but at the same time allows some water as a liquid or vapor to permeate into the membrane to combine with the oxidant, (for example, $H_2O+I_2\rightarrow HOI+HI$) while protecting the anode surface below. The membrane may also include a porous hydrophobic outer surface 28 of the same or a different material. Preferred characteristics of the surface 28 are that it allows transport of moisture from the environment there through so the moisture can react with the oxidant, and the oxidant in its generated form before and after reaction with the moisture can be transported through the surface to react with the contaminant. The surface should be chemically stable so that it does not react with the oxidant or the external contaminant. It should also be washable with common cleaning solutions and resistant to water (hydrophobic) while at the same time preventing penetration by those liquids to allow damage of the lower layers. As an added feature, the surface may include a chemical, bio- or photocatalyst to aid in the decomposition of contaminants that contact the surface.

There are several ways to expose an electrochemical cell to a controlled flow of electrons by applying a DC or AC bias across the cell. The cell 12 can be connected to a switched (i.e., on-off) power source 24 which, when switched on, creates an electron flow through the electrochemical cell 12. Alternatively the anode 20 can be photo-activated (i.e., a photocell) or heat-activated, causing electrons to flow when exposed to light or heat, respectively. A non-limiting example of a heat-activated sensor 26 could be a thermocouple for detecting increased heat production in viable cells or skin (e.g. to detect the onset of a fever after infection). The coated device, structure or substrate 10 can also include one or more sensors 26 capable of detecting chemical or biological agents, which, upon exposure to that agent can activate a shunt and/or the power source 24 causing current to flow through the multi-layered electrochemical cell 12 structure, thus producing or releasing the oxidant at the anode, which, in turn, can chemically oxidize the agent, deactivating or decomposing the agent. Alternatively, solar radiation incident on the light-activated anode 20 can generate electron flow photochemically releasing the oxidants. The decomposition/generation rate of the oxidant is generally dependent on the level (amount) of current applied and the direction of current flow, i.e., the greater the current applied the greater the flow of oxidant generated.

Heating the cell surface causes electrogenerated oxidants to diffuse to/into contaminants more quickly, and additionally can cause contaminants to undergo phase transitions that render them easier to kill. [See Alimova et al., *Proteins and Dipicolinic Acid Released During Heat Shock Activation of Bacillus Subtilis Spores Probed by Optical Spectroscopy*, Applied Optics, Vol. 45, 2006, Pgs. 445-450.] Therefore, heating the cell surface prior to electrolysis can 'tenderize' very hardy microorganisms like bacterial spores, thereby facilitating the decontamination of resistant contaminants. Heating the cell surface of the present invention to about 55° C. for about one hour prior to electrolysis, for example, can enable the cell to destroy monolayer coverages of *Bacillus cereus* spores on the surface. The surface can be heated in a number of ways, including without limitation resistive heating achieved by passing current through the top layer (anode) only. After the pre-heating step, the current can then be switched so that it flows between the two electrodes as usual. The effective time and temperature range for this type of pre-treatment may depend upon the type of contaminant being targeted. In one embodiment of the present invention, the effective temperature range for resistive heating can be from about 20° C. to about 90° C.

The present invention may be used to deactivate a number of biological warfare (BW) agents including without limitation viruses, bacteria such as *Bacillus anthracis*, fungi, unicellular parasites and biologically generated toxins such as botulinum toxin (which causes botulism) in any form (including sporulated bacteria). Similarly, the invention could be used to treat chemical warfare (CW) agents including without limitation nerve agents such as Soman (GD) or methylphosphonothioic acid (VX) and blister or vesicants agents such as Sulfur Mustard/Yperite (HD), as well as other hazardous compounds such as nitriles, BZ (3-quinuclidinyl benzilate), and malathion. Gas chromatography/mass spectroscopy studies have shown, for example, that iodine vapor can decompose dimethyl methyl phosphonate (DMMP), a simulant for a class of chemical warfare agents.

Figure 2A:
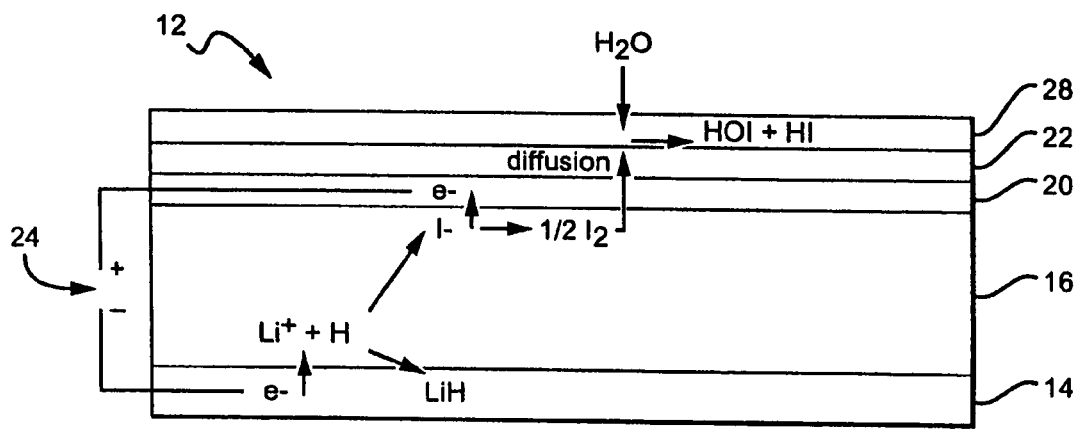
FIGS. 2a and 2b are schematic drawings of the assembly of FIG. 1 illustrating the operation of two embodiments of an electrochemical cell for decontamination of an assembly following exposure to a contaminant.
Figure 2B:
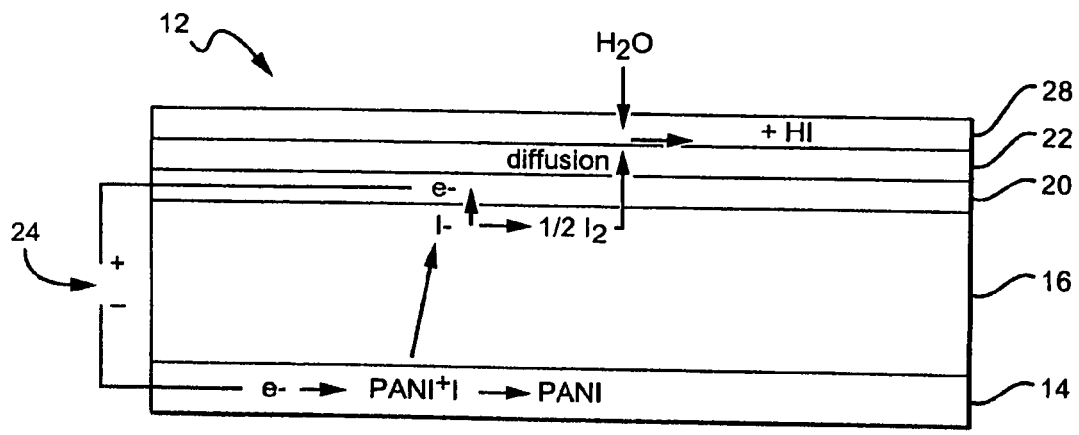

FIGS. 2a and 2b are schematic drawings illustrating the chemical reactions in two embodiments of the electrochemical cell 12. FIG. 2a utilizes a LiI/HI system; FIG. 2b uses a PANI source. Once activated, electrons flowing from the power source 24 (or the photocell/anode 20) connected to the electrochemical cell 12 causes oxidation of the iodide in the electrolyte layer 16 and/or cathode 14 to elemental iodine ($I_2$) which permeates through the anode to the porous hydrophobic surface 22 where it combines with moisture from the environment and disproportionates according to the formula:

$$I_2 + 2H_2O \rightarrow H^+ + I^- + HOI$$

A typical power source may provide 5V at 1-10 milli-amp/$cm^2$, preferably about 10 milli-amp/$cm^2$. The HOI (I has a +1 valence) can then react with the contaminating agent in contact with the surface layer 22, 28 of the electrochemical cell 12 on the substrate 10. A loading of about $3\%_w$ of iodine per $cm^2$ of coated surface (provided as an iodide) can provide a continuous flow of a decontaminating agent to the cell surface 28 for about two hours of continuous activation. A typical loading may be from about 1 mg/$cm^2$ to at least about 10 mg/$cm^2$.

EXAMPLES

Example 1

An experimental cell constructed as in FIG. 2b with PANI iodide cathode, an electrolyte containing EC, PC, PAN, TPAI (34:50:7.77:7.77 by weight), a Teflon fabric separator and a platinized carbon anode was polarized with a positive voltage applied to the anode vs the cathode for five minute intervals.

Iodine flowing from the coating was detected by exposure to a disk of Watman #44 filter paper which was previously soaked in 0.5 M KI and then dried. A 6 mm diameter disk cut from the paper was placed over the multilayer coating to react with the evolving elemental iodine. The reaction immobilized the evolved $I_2$ vapor as brown $KI_3$ product within the paper through the reaction:

$$\tfrac{1}{2}I_2(gas) + KI(solid) \rightarrow KI_3(solid)$$

Subsequently, the exposed disk containing immobilized elemental iodine developed an intense blue color when placed in a test tube to which was added 2 mL of 1% starch solution (Aldrich 319554). Iodide (I), in contrast, develops no color. The blue color developed by the reaction of the starch indicator with the filter-paper disks exposed for 10 minute periods darkened as bias increased, evidencing an increase iodine output. Using this method, the blue indicator was observed for nine sequential 10 minute exposures at 3 V. The iodine continued to evolve for 90 minutes of accumulated activation.

Example 2

A first example of a layered electrochemical cell uses a cathode 14 containing a combination of Ketjen black (an oil furnace carbon black) and PANT iodide, preferably $21\%_w$ Ketjen black and $79\%_w$ PANI iodide, and an electrolyte layer 16 comprising a polyacrylonitrile (PAN) gel 17, from about 7 to about 8% tetrapropyl ammonium iodide (TPAI) 18, from about 33 to about $34\%_w$ ethylene carbonate (EC), from about 48 to about $50\%_w$ of propylene carbonate (PC) and from about 8 to about $12\%_w$ of PAN.

The anode 20 contained platinized carbon with a PVA (Polyvinyl alcohol) binder, platinized woven carbon fabric, or a platinized carbon fiber tissue (obtained from Tech Fiber Products), preferably about $1\%_w$ Pt in carbon. The surface covering/membrane 22, 28 was a hydrophobic porous membrane or microporous filter paper, typically coated with a polyurethane or a fluorocarbon formed of Teflon®, Fluorothane™ or Sartech H. As an alternative, a Teflon separator may also be placed between the electrolyte and the anode and Ag or activated $TiO_2$ may be added to the surface coating/membrane.

Example 3

A second example of the layered electrochemical cell 12 contains:

1) a cathode 14 containing a coating formed from a paste of ground 2,5 dimercapto-1,3,4 thiadiazole, a conducting polymer such as set forth in U.S. Pat. No. 5,665,492, dispersed in a carrier liquid, forming a flowable liquid that is painted on the device, structure or substrate. Alternatively, polyanaline iodide (PANI iodide) can be electrodeposited or otherwise deposited on the surface. As a third alternative, Prussian Blue can be electrodeposited on the substrate or dispersed in a carrier liquid and painted on the surface.
2) The electrolyte layer 16 contains a hydrophobic ionic layer which includes a halide containing compound 18, for example KI or other solid or gel electrolyte containing KI.
3) The anode 20 may be a porous, solid conductor which can be formed from a slurry or dispersion of carbon black, platinized carbon black or Pd metallized $TiO_2$. The anode 20 may also include a photosensitizer such as Ru(II)bipyridyl (e.g. N719, available from Solaronix SA, Switzerland).
4) A porous hydrophobic surface layer 22 can then provided by a fluorocarbon polymer.

Examples illustrating preparation of several of the components are as follows:

PANI Iodide. PANI iodide was prepared by forming a slurry of 3 gm. of the oxidized form of PANI (emeraldine base) in an excess of 1 M HI in deionized water and mixing for 16 hours with stirring. The mixture was filtered and the PANI iodide residue was recovered and washed with cold deionized water.

Electrolyte. A mixture 33.33 parts ethylene carbonate (CAS 96-49-1), 48.39 parts propylene carbonate (CAS 108-32-7), 7.53 parts tetrapropylammonium iodide (CAS 631-40-3) and between 7.53 and 10.75 parts polyacrylonitrile (CAS 25014-41-9) was heated in a water bath at 85-90° C. to form a solution suitable for casting or spreading on the solid substrate to form a thin film. Alternatively the solution was used to saturate a cloth formed of a dielectric material. The resulting liquid formed a gel within three days and was completely gelled within a week. The electrolyte film can be formed on a surface or within a porous fabric, such as an open weave Teflon separator. However, this application technique is merely representative and any approach that results in an ionically conducting solid or gelled electrolyte film containing the precursor to the oxidant (iodide in this example) can be used.

Cathode. 0.265 gm of Ketjen black (carbon), 0.9937 gm of PANI iodide (prepared as above) were mixed with 12.256 gm of N-methylpyrrolidone (NMP) with sonication. The resulting mixture formed an ink that was painted on the substrate and heated to 80-100° C. for 1 hour to dry and cure. When the cathode was applied to a non-conducting surface provision is made to contact the cathode with a copper foil adhesive tape (3M Cu conductive tape) lead. The lead was over-coated with a uv cured epoxy to assure good contact.

Anode. Anodes were prepared by dipping a conducting carbon fabric in a chloro-platinic acid solution for 5 minutes. The wetted fabric was dried at 90° C. and then heated in a furnace at 300° C. for 5 minutes. The anode can then be coated with a thin hydrophobic lacquer such as Sartech H or Fluorothane™. However, other hydrophobic coatings can also be used.

Coating Assembly. On any substrate the cathode is applied using common coating techniques, a conductive lead is attached and then a layer of electrolyte is applied. The electrolyte may be contained in a highly porous dielectric fabric separator. While the electrolyte is still a liquid, the anode is placed on the surface and a copper tape lead is also attached to the anode.

Hydrophobic Top Coating. After the cell is completely assembled, a porous hydrophobic coating or film is applied such as by overlaying a microporous filter paper film or coating with Sartech H or Fluorothane™. Other thin, porous hydrophobic coatings can be considered, but a hydrophobic (or superhydrophobic) and biocidally active coating that passes elemental iodine is preferred. A porous hydrophobic or superhydrophobic will impede the passage of liquid water, but allow water vapor to pass. A superhydrophobic surface can be obtained by providing a roughed hydrophobic surface or coating a roughened surface with a hydrophobic material which increases the contact angle between a water droplet and the non-wettable surface on which it rests. Alternatively, the top coat can be applied to the anode during the anode assembly, as described above.

Cell Capacity. The typical weight of the active component of the electrolyte is 0.01 gm $TPAI/cm^2$ of film. This is equivalent to (0.01 gm/313.27 gm/mol) mol. TPAI or a theoretical capacity of (0.01 gm/616.54 gm/mol~16 μmol) $I_2$. Experiment results show that *Escherichia coli* 0157H:7 can be killed in 300 sec or less at an average current density of 0.001 A/cm2. From Faraday's Law, this quantity of charge corresponds to 0.3 coul. or 1.6 μmol of $I_2$, assuming a 100% current efficiency for the $I_2$ production. Hence, the cell can provide 10 cycles of kills using such an assumption of efficiency. It is unlikely that the efficiency for $I_2$ production is 100%. Therefore the observed kill likely used substantially less $I_2$ than that indicated by the total charge passed. The 10 cycles estimate represents a lower limit for the number of kills for this microbe. It is likely that the number of practical cycles is considerably greater since the true current efficiency of the cell remains low. Furthermore, the capacity of the cell can be increased by using a thicker electrolyte film having optimized or greater iodide loading. Data indicates that several μcoul can generate sufficient quantities of $I_2$ as evidenced by complete staining of a piece of filter paper with KI/starch indicator.

In each instance, following activation and depletion of the oxidizer precursor content in the electrochemical cell, the cell can be reactivated by depositing fresh precursor. Alternatively, in some situations, the cell could be reactivated by depositing a halogen solution on the surface 28 followed by applying a reverse polarization to the cell.

Figure 3:
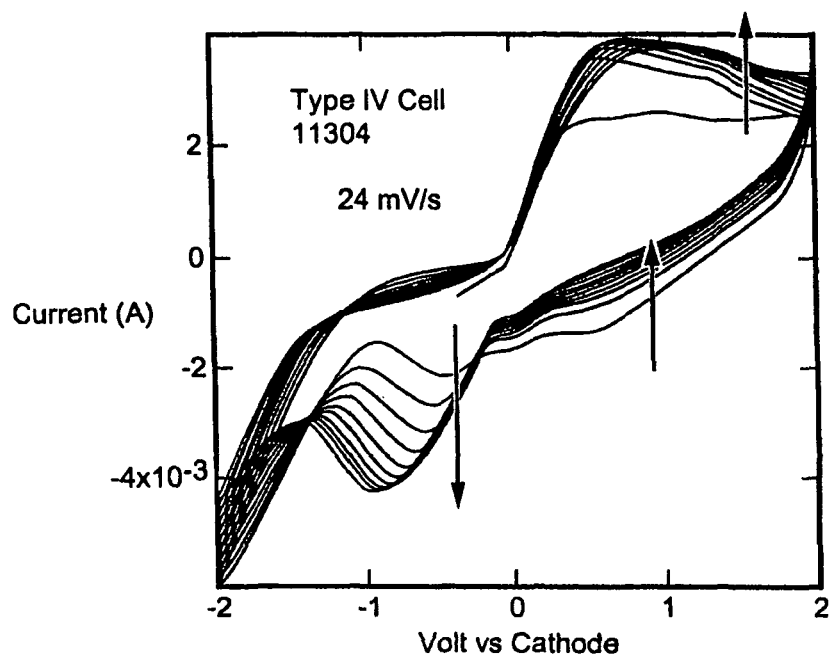
FIG. 3 is a graph showing the recycle curve for an electrochemical cell as shown in FIG. 1.
Figure 4:
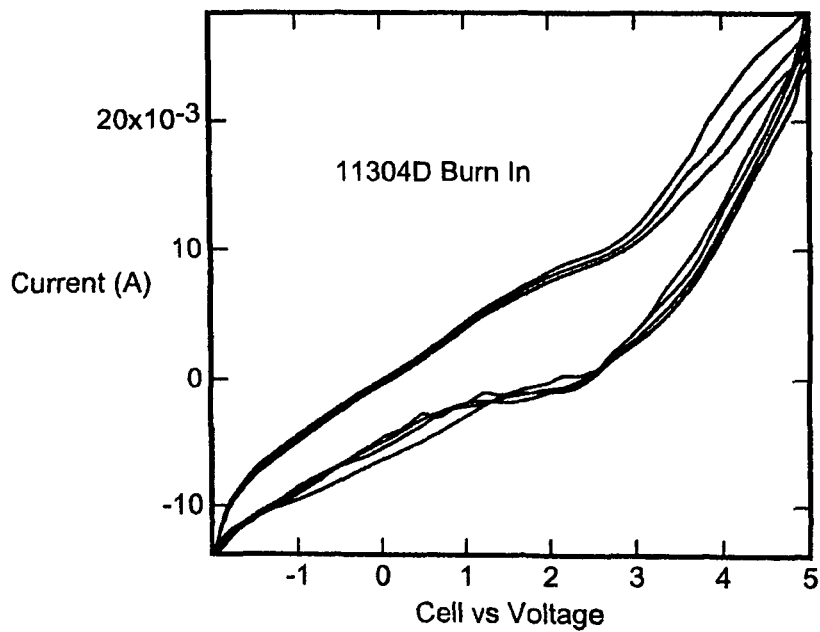
FIG. 4 is a graph showing the recycle curve for a different cell of the same construction.
Figure 5:
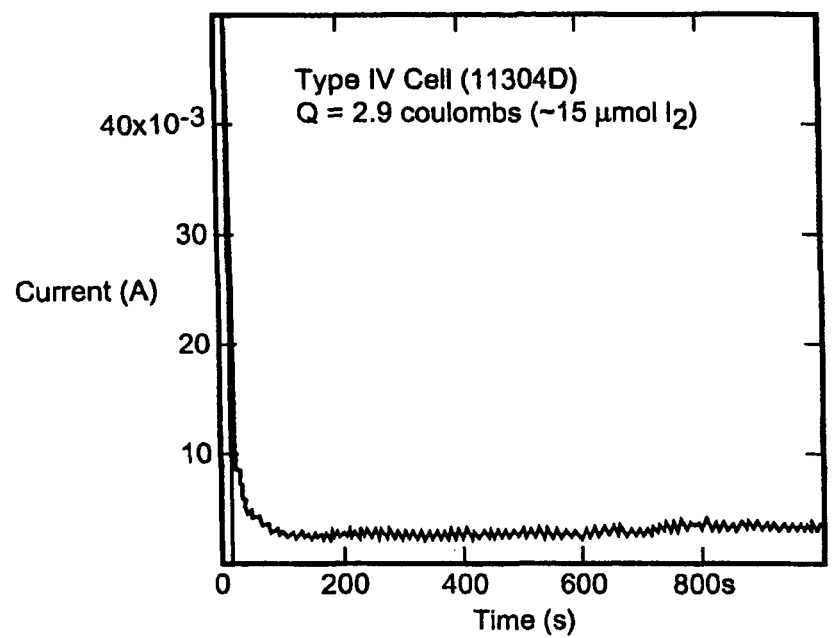
FIG. 5 is a graph showing the current flow for continuous operation of an electrochemical cell.

FIG. 3 is a graph showing the recycle curve for an electrochemical cell comprising the carbon black/PANI cathode, the TPAI/PAN electrolyte, a platinized carbon fiber anode and a Sartech H membrane as described above operated at 5V. Delivery of iodine to the surface occurs with positive current flow and ceases when the current flow is reversed. FIG. 4 is a graph showing the recycle curve for the burn in of a different cell of the same construction FIG. 5 is a graph showing the current flow for continuous operation of an electrochemical cell, the cell having the same construction as that used to generate the graph of FIG. 3, containing about 15 μmols of $I_2$. While this graph only illustrates operation for 1000 seconds (approximately 17 minutes), there is a continuous flow of $I_2$ for at least 1 hour.

Figure 6:
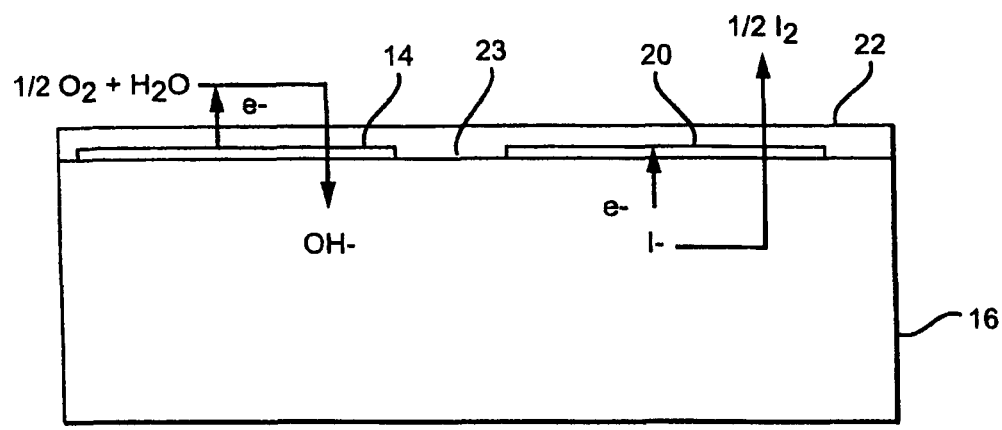
FIG. 6 is a schematic drawing of a device having coplander electrodes.

FIG. 6 shows an alternative embodiment which includes an electrolyte 16 with the anode 20 and cathode 14 both being located on the same surface of the electrolyte layer 16 but spaced apart to form a space or gap 23 therebetween with the porous surface layer 22 covering the anode 20 and cathode 14 and filling the space or gap 23 between them. A typical gap 23 is from about 0.001 mm to about 0.5 mm, preferably, from about 0.05 to about 0.25 mm. In a preferred embodiment of this construction the cathode 14 is an air cathode. In a further variation the anode 20 and cathode 14 can be inter-digitated, but still spaced apart as shown in the top view of FIG. 7. Moisture and oxygen from the surrounding atmosphere passes through the porous surface layer 22 to cathode 14, causing electrons to flow through the electrolyte layer 16 and the oxidant to be released from the anode 20, cathode 14 or electrolyte 16 which contains the oxidant precursor. The anode 20 can contain materials as discussed hereinabove. Suitable materials for construction of an air cathode are those typically used in fuel cells. Examples include, but are not limited to platinum, platinized carbon, platinized titanium, conducting oxides and conducting polymers such as PANI.

Figure 8:
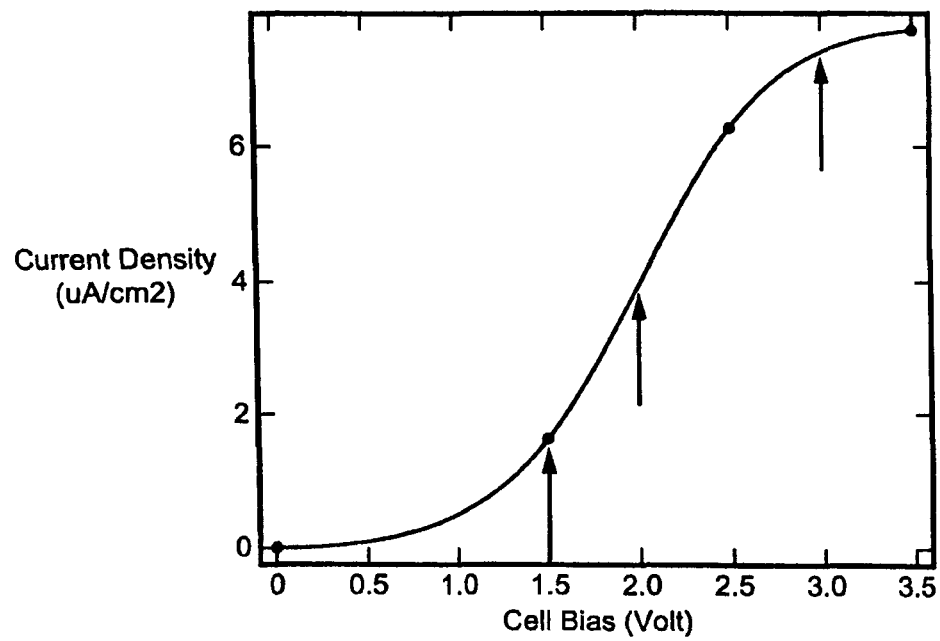
FIG. 8 is a graph of cell bias vs. current density for a typical device incorporating features of the invention.

FIG. 8 is a graph of applied voltage (cell bias) vs. current density for a typical cell incorporating features of the invention. To demonstrate evolution of iodine from the surface of the cell suitable iodine collectors, such as a sheet of filter paper as described above, were placed on the device surface, and exposed to gases generated at the surface at various applied voltages (as indicated by the arrows on FIG. 8) to collect evolving gases for a predetermined period of time, the quantity of iodine produced being indicated by reaction with a starch solution. If iodine is present a reaction occurs between the iodine and the starch and a colored stain appears on the paper, the quantity of iodine being qualitatively shown by the amount of color (darkness) of the stain produced. The cell used to generate the curve of FIG. 8 appears to have a threshold potential of about 2 volts. Below about 2 volts no iodine appears to evolve. At 3 volts a significant quantity of iodine is continuously generated, as evidenced by a dark stain. At voltages between 2 and 3 increasing amounts of iodine continuously evolve as evidenced by a gradient of staining, from very light to dark obtained at about 3 volts or greater.

The threshold appears to depend on cell geometry, electrolyte conductivity and cell iodine concentration. Iodine evolution appears to be time dependent with the total evolved iodine being primarily dependent on the quantity in the cell and the amount evolving on a per time basis (i.e., per minute) depending primarily on the cell bias in excess of the threshold voltage, applied to the cell. The lower the applied voltage, the slower the iodine can evolve.

Figure 7:
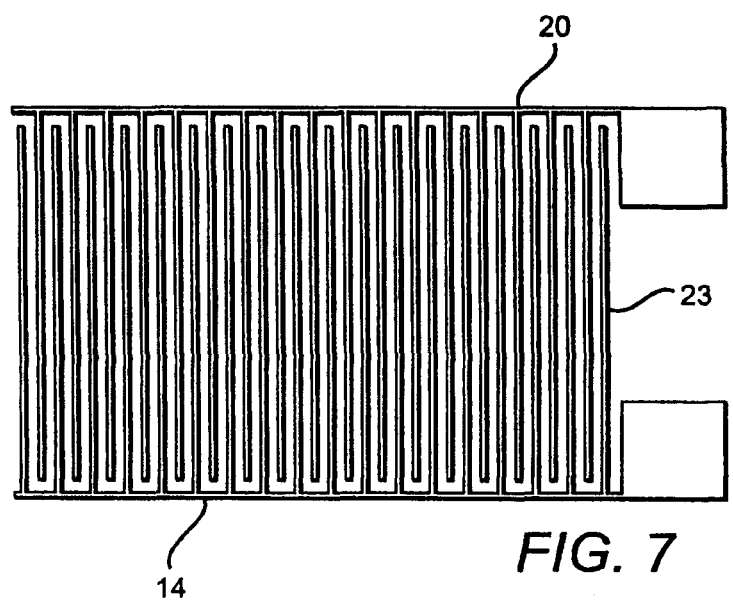
FIG. 7 is a top view of a device as shown in FIG. 6 where the electrodes are interdigitated.
Figure 9:
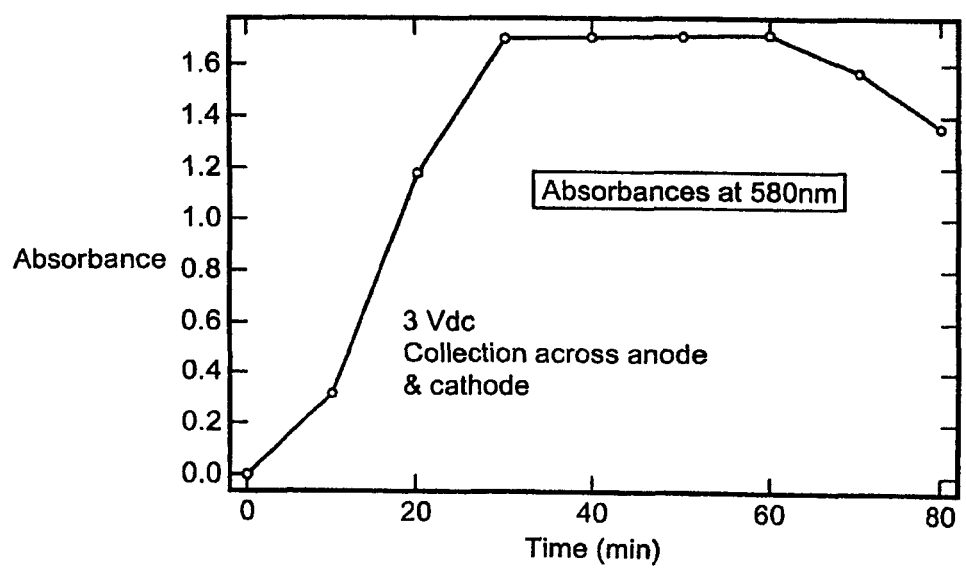
FIG. 9 is a graph showing the time dependent evolution of iodine for a typical cell in accordance with FIGS. 6 and 7 at 3 volt bias.

FIG. 9 is a graph showing the evolution of iodine from the surface of an interdigitated cell as shown in FIGS. 6 and 7 over a period of 80 minutes, the amount of iodine evolving over the 80 minute period being indicated by UV-VIS absorption at 580 nm measured for the starch/iodine complex at selected intervals in that time period. There appears to be a time delay of about 20 minutes until a relatively stable iodine evolution is obtained, but thereafter, until the iodine in the cell is dissipated, there appears to be a relatively stable evolution of iodine for about one hour at a cell bias of about 3V.

A first preferred embodiment of the self-decontaminating surface described herein includes depositing a carbon-PANI-iodine coating on a metal substrate followed by the electrolyte and the porous anode. An alternative construction utilizes a flexible cloth or blanket of material comprising a porous carbon felt soaked with PANI-iodide to form the cathode followed by a layer of the electrolyte and then a porous carbon felt anode. Furthermore, a structure comprising a porous felt anode, an electrolyte, a PANI-iodide soaked felt cathode, an electrolyte, and a porous felt anode can be fabricated with leads on the respective anodes and cathode. The cloth can then be rolled up or pleated to provide a high surface area structure which can serve as an active filter and generate decontaminating agent for an enclosed environment, including for example a flow-through filter.

Figure 10:
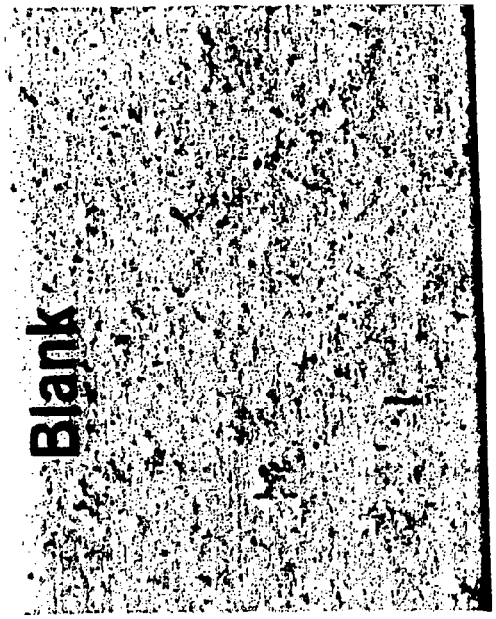
FIG. 10 is a photo micrograph showing an *Escherichia coli* contaminated surface after exposure to iodine produced by an assembly as in FIG. 1.
Figure 11:
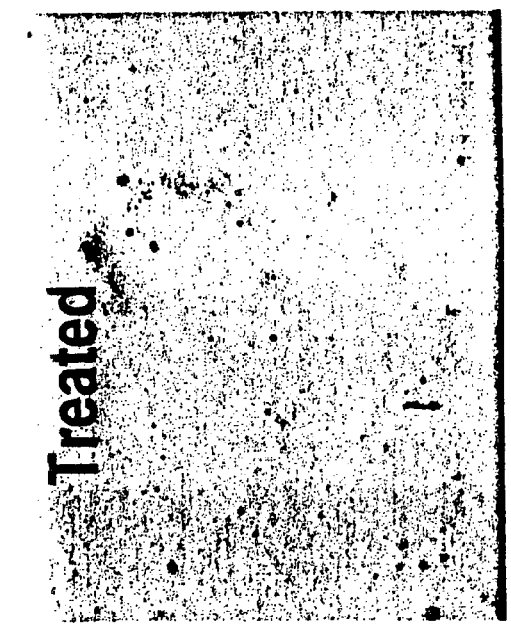
FIG. 11 is a photo micrograph of an *Escherichia coli* contaminated surface without treatment as set forth herein.
Figure 12:
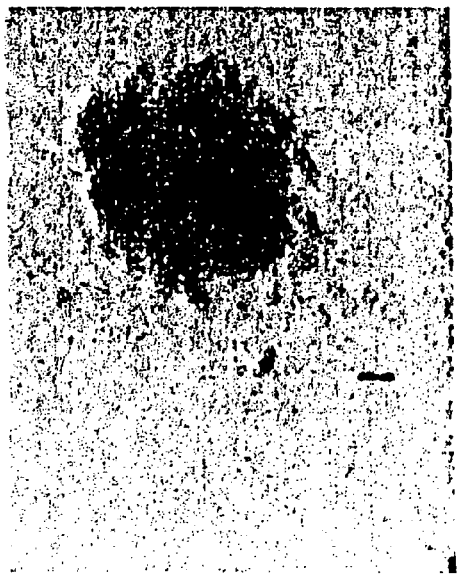
FIG. 12 is a photo micrograph of dead *Bacillus subtilis* cells on a surface following treatment as set forth herein.

FIGS. 10-12 illustrate the effectiveness of devices incorporating features of the invention in destroying biological contaminants deposited on the surface of the cell. FIG. 10 shows a carbon felt anode surface incorporating features of the invention following contamination with *Escherichia coli*, treatment for 1 hour at 5V and 2.9 coulombs (releasing approximately 15 µmol $I_2$ as estimated using the Faraday equation assuming 100% efficiency for the electrochemical conversion), and then incubation for 24 hours, FIG. 11 shows a similar contaminated surface without release of $I_2$. Subsequent experiments with optimized anodes showed that times as short as several minutes (i.e. great than about 5 minutes) were sufficient to kill the *Escherichia coli*. FIG. 12 shows dead cells on a surface incorporating features of the invention contaminated with *Bacillus subtilis* and decontaminated for a period of 1 hour as described herein. Both vegetative cells and spores were killed by the treatment.

The embodiments and examples set forth herein were presented to explain the nature of the present invention and its practical application, and thereby to enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. While the incorporation of halogen salts or compounds which can electrochemically release halogen oxidants is described herein, for example, the invention contemplated is not so limited. One skilled in the art will recognize that other compounds may be used in the same structural arrangement to electrochemically release a decontaminating oxidant on demand, particularly to decontaminate sensitive equipment or surfaces such as electronic devices or human skin. These include, but are not limited to, peroxides, ammonia, permanganates and other known electrochemically generated oxidizing agents. Similarly, the dimensions, structure, or configuration of other system components may vary and accordingly are not to be construed as limiting the scope of the invention.

We claim:

1. A flexible, free standing decontamination device comprising an electrochemical cell comprising:
   an anode and a cathode; an electrolyte between said anode and cathode comprising at least one precursor for an oxidizing reagent, the oxidizing reagent comprising a halogen;
   a porous surface layer on and distinct from said anode, said porous surface layer comprising a permeable film or membrane; and
   a means for heating said porous surface layer;
   the at least one precursor electrochemically releasing the oxidizing reagent, and
   the oxidizing reagent effective for decontaminating an external surface or adjacent enclosed space exposed to a contaminating biological or chemical agent.

2. The device of claim 1, wherein the oxidizing reagent is provided on demand.

3. The device of claim 2, wherein the device is activated by a controlled flow of electrons and the precursor, on exposure to the controlled flow of electrons, reacts electrochemically to release the oxidizing reagent.

4. The device of claim 1, wherein the oxidizing reagent comprises iodine.

5. The device of claim 1, wherein the electrochemical cell comprises:
a cathode comprising flexible material;
an electrolyte layer on the surface of the cathode; and
an anode comprising flexible material.

6. The device of claim 5, wherein the flexible material in at least one of the anode and the cathode comprises porous carbon felt.

7. The device of claim 5, wherein the cathode is a depolarizable cathode.

8. The device of claim 5 wherein the electrochemical cell is formed into a rolled or pleated structure.

9. A surface comprising at least one device according to claim 1.

10. An enclosed space comprising at least one device according to claim 1, wherein the space does not comprise a liquid.

11. The device of claim 1, wherein the oxidizing reagent is selected from the group consisting of a molecular halogen, a polyhalide anion, a halogen cation, a hypohalite, and combinations thereof.

12. The device of claim 1, wherein said porous surface layer is hydrophobic or includes a hydrophobic or partially hydrophobic surface coating.

13. The device of claim 1, wherein said means for heating said porous surface layer comprises passing a current through said anode.

14. A flexible, free standing decontamination device comprising an electrochemical cell comprising:
an anode and a cathode; an electrolyte between said anode and cathode comprising at least one precursor for an oxidizing reagent, the oxidizing reagent comprising a halogen;
a porous surface layer on and distinct from said anode, said porous surface layer comprising a permeable film or membrane;
the at least one precursor electrochemically releasing the oxidizing reagent, and
the oxidizing reagent effective for decontaminating an external surface or adjacent enclosed space exposed to a contaminating biological or chemical agent;
wherein the oxidizing reagent is provided on demand;
wherein the device is activated by a controlled flow of electrons and the precursor, on exposure to the controlled flow of electrons, reacts electrochemically to release the oxidizing reagent; and
wherein said anode is arranged to be photo- or heat-activated such that said controlled flow of electrons is created when said anode is exposed to sufficient light or heat, respectively.

15. A flexible, free standing decontamination device comprising an electrochemical cell, said cell comprising:
a cathode layer;
an electrolyte layer on said cathode, comprising at least one precursor for an oxidizing reagent, the oxidizing reagent comprising a halogen;
an anode layer on said electrolyte layer;
a porous surface layer on and distinct from said anode, said porous surface layer comprising a permeable film or membrane; and
a means for heating said porous surface layer;
the at least one precursor electrochemically releasing the oxidizing reagent, and
the oxidizing reagent effective for decontaminating an external surface or adjacent enclosed space exposed to a contaminating biological or chemical agent.

* * * * *